(12) United States Patent
Ballegoy et al.

(10) Patent No.: US 9,597,670 B2
(45) Date of Patent: Mar. 21, 2017

(54) CATALYST AND ISOMERISATION PROCESS

(75) Inventors: Carolus Maria Ballegoy, Amsterdam (NL); Dinyar Khushroo Captain, Amsterdam (NL); Joseph Cornelis Van Giezen, Amsterdam (NL); Lucas Petrus Simon Keyzer, Amsterdam (NL); Nicoleta Cristina Nenu, Amsterdam (NL); Ingrid Maria Van Vegchel, Amsterdam (NL)

(73) Assignee: SHELL OIL COMPANY, Houston, TX (US)

( * ) Notice: Subject to any disclaimer, the term of this patent is extended or adjusted under 35 U.S.C. 154(b) by 496 days.

(21) Appl. No.: 13/002,381

(22) PCT Filed: Jun. 24, 2009

(86) PCT No.: PCT/EP2009/057862
§ 371 (c)(1),
(2), (4) Date: Sep. 11, 2012

(87) PCT Pub. No.: WO2010/000652
PCT Pub. Date: Jan. 7, 2010

(65) Prior Publication Data
US 2013/0041194 A1    Feb. 14, 2013

(30) Foreign Application Priority Data
Jul. 4, 2008 (EP) .................................. 08159696

(51) Int. Cl.
| | | |
|---|---|---|
| B01J 29/06 | (2006.01) | |
| B01J 29/74 | (2006.01) | |
| B01J 29/76 | (2006.01) | |
| C07C 5/27 | (2006.01) | |
| B01J 35/02 | (2006.01) | |
| B01J 29/72 | (2006.01) | |
| B01J 35/00 | (2006.01) | |
| B01J 35/10 | (2006.01) | |

(52) U.S. Cl.
CPC ....... *B01J 29/7469* (2013.01); *B01J 29/7669* (2013.01); *C07C 5/2754* (2013.01); *C07C 5/2791* (2013.01); *B01J 29/7269* (2013.01); *B01J 35/0026* (2013.01); *B01J 35/023* (2013.01); *B01J 35/1019* (2013.01); *B01J 35/1042* (2013.01); *B01J 35/1047* (2013.01); *B01J 35/1061* (2013.01); *B01J 2229/16* (2013.01); *B01J 2229/20* (2013.01); *B01J 2229/42* (2013.01); *C07C 2529/70* (2013.01); *C07C 2529/72* (2013.01); *C07C 2529/74* (2013.01); *C07C 2529/76* (2013.01); *Y02P 20/52* (2015.11)

(58) Field of Classification Search
USPC .................................. 502/60, 63, 64, 66, 74
See application file for complete search history.

(56) References Cited

U.S. PATENT DOCUMENTS

| | | | |
|---|---|---|---|
| 3,832,449 A | 8/1974 | Rosinski et al. | |
| 3,856,872 A | 12/1974 | Morrison ................. | 260/668 A |
| 4,152,363 A * | 5/1979 | Tabak ................... | C07C 5/2729 502/64 |
| 4,159,282 A * | 6/1979 | Olson et al. .................. | 585/481 |
| 4,278,565 A * | 7/1981 | Chen et al. .................... | 502/74 |
| 4,485,185 A | 11/1984 | Onodera et al. ................ | 502/71 |
| 4,762,957 A | 8/1988 | Sachtler et al. .............. | 585/481 |
| 4,874,504 A | 10/1989 | von Ballmoos et al. | |
| 4,899,012 A * | 2/1990 | Sachtler et al. ............. | 585/482 |
| 4,939,110 A | 7/1990 | Sachtler et al. ................ | 502/66 |
| 4,962,259 A * | 10/1990 | Sachtler et al. ............. | 585/480 |
| 5,053,558 A | 10/1991 | Sachtler et al. | |
| 6,207,871 B1 | 3/2001 | Hellring et al. | |
| 6,576,120 B1 | 6/2003 | Van Ballegoy et al. | |
| 6,652,832 B2 * | 11/2003 | Malek .......................... | 423/706 |
| 6,709,570 B1 | 3/2004 | van Crijnen-Beers et al. | |
| 7,244,510 B2 | 7/2007 | van Den Abbeele et al. | |
| 7,368,620 B2 | 5/2008 | Zhou et al. | |
| 8,030,239 B2 | 10/2011 | Oh et al. | |
| 9,199,894 B2 | 12/2015 | Nenu et al. | |
| 2006/0030478 A1 | 2/2006 | Raich et al. | |
| 2007/0004947 A1 | 1/2007 | Zhou et al. | |

(Continued)

FOREIGN PATENT DOCUMENTS

| | | |
|---|---|---|
| CN | 1330699 | 1/2002 |
| CN | 1376089 | 10/2002 |

(Continued)

OTHER PUBLICATIONS

Zhang W et al: "Dealuminated zeolite-based composite catalysts for reforming of an industrial naphthene-rich feedstock", Applied Catalysis A: General, Elsevier Science, Amsterdam, NL, vol. 168, No. 1, Mar. 13, 1998, pp. 113-130, XP004271341.

Smirniotis P.G., et al: "Effect of the Si/Al Ration and of the Zeolite Structure on the Performance of Dealuminated Zeolites for the Reforming of Hydrocarbon Mixtures", Ind. Eng. Chem. Res., vol. 35, No. 9, 1996, pp. 3055-3066 XP002510706.

Miller, J. T. et al., "A Fundamental Study of Platinum Tetraammine Impregnation of Silica 2. The Effect of Method of Preparation, Loading and Calcination Temperature on (reduced) Particle Size", Journal of Catalysis, vol. 225, 2004, pp. 203-212.

(Continued)

*Primary Examiner* — Elizabeth Wood
(74) *Attorney, Agent, or Firm* — Charles W. Stewart

(57) ABSTRACT

An alkylaromatics isomerisation catalyst, which catalyst comprises at least 50 wt % of an inorganic binder; at least 0.01 wt % of a Group VIII metal and 1-9 wt % ZSM-12 zeolite wherein the silica to alumina molar ratio (SAR) of the ZSM-12 zeolite is in the range of from 60 to 200, and a process for the isomerisation of alkylaromatics to provide a reaction mixture, said process comprising contacting a hydrocarbon stream comprising alkylaromatics with such catalyst.

19 Claims, 5 Drawing Sheets

(56) References Cited

U.S. PATENT DOCUMENTS

2008/0035525 A1 2/2008 Burgfels et al.

FOREIGN PATENT DOCUMENTS

| CN | 1715370 | 1/2006 | | |
|---|---|---|---|---|
| CN | 101208283 | 6/2008 | | |
| CN | 101541419 | 9/2009 | | |
| EP | 1547684 | 6/2005 | | |
| WO | WO9745198 | 12/1997 | ............. | B01J 29/80 |
| WO | WO2004046034 | 6/2004 | ............. | C01B 39/42 |
| WO | 2010000652 | 1/2010 | | |

OTHER PUBLICATIONS

PCT International Search Report, Application No. PCT/EP2011/070193 dated Feb. 6, 2012.
State Intellectual Property Office of the People's Republic of China, 1st Office Action dated Jun. 19, 2014, Chinease Application No. 201180062617.0.
Spieker, W. A. et al., "A Fundamental Model of Platinum Impregnation Onto Alumina", Chemical Engineering Science, vol. 56, 2001, pp. 3491-3504.

* cited by examiner

CATALYST AND ISOMERISATION PROCESS

PRIORITY CLAIM

The present application claims priority of European Patent Application No. 08159696.7 filed Jul. 4, 2008.

This invention relates to a zeolite-based catalyst for the isomerisation of alkylaromatics, more specifically ethylbenzene, particularly to increase the production of xylenes from a hydrocarbon fraction containing aromatic hydrocarbons containing 8 carbon atoms.

Following fractionation or distillation of crude petroleum oil, a straight-run naphtha fraction, boiling in the 70° C. to 190° C. range, is obtained. This fraction may be catalytically converted to an aromatic reformate.

On conversion to reformate, the aromatics content is considerably increased and the resulting hydrocarbon mixture becomes highly desirable as a source of valuable chemical intermediates and as a component for gasoline.

Reformate generally contains aromatic hydrocarbons having 8 carbon atoms including but not limited to ethylbenzene and xylenes. Other components may be present such as their hydrogenated homologues such as naphthenes.

Within the xylenes, para-xylene is the most useful commodity and isomerisation or transalkylation processes have been developed to increase the proportion of para-xylene ("pX"). However, isomerisation or transalkylation processes can also produce undesired side-products such as compounds having of from 1 to 5 carbon atoms, toluene, compounds having 9 or more carbon atoms and benzene.

Many catalysts have been made and proposed for various reactions involving aromatics, but for some reactions, such as ethylbenzene isomerisation or transalkylation processes, there is commonly a trade-off between providing the desired products and known side reactions. One common side reaction of ethylbenzene hydroisomerisation is the formation of compounds having of from 1 to 5 carbon atoms, which, if flared, create carbon dioxide, which is disadvantageous from an environmental point of view. One conventional way to avoid producing a large amount of compounds having of from 1 to 5 carbon atoms and carbon dioxide, is to limit the amount of ethylbenzene reactant. However, this then limits the yield of the desired xylenes.

U.S. Pat. No. 4,939,110 discloses a catalyst comprising an inorganic oxide binder, a pentasil zeolite, a Group VIII metal and lead for use in the conversion of aromatic hydrocarbons.

U.S. Pat. No. 4,762,957 discloses a process for the isomerisation of alkylaromatics using a catalyst with an alumina matrix, a magnesium-containing zeolite, and a Group VIII metal component.

Whilst reasonable results are presented in these documents, the inclusion of magnesium or iron adds complexity and expense to the catalyst preparation.

WO 97/45198 A1 discloses a zeolite bound zeolite catalyst for use in hydrocarbon conversion comprising first crystals of a first zeolite, and a binder comprising second crystals of a second zeolite which has a structure type that is different from the structure type of the first zeolite. The first and second zeolites provide a bifunctional catalyst having the capability of performing two or more functions. However, the production of such a zeolite bound zeolite catalyst requires additional complexity and manufacturing steps, so that zeolite bound zeolite catalysts have not apparently been scaled up commercially.

U.S. Pat. No. 3,856,872 describes a xylene isomerization process in which the conventional platinum on silica-alumina is replaced by a zeolite catalyst of the ZSM-5 type or a zeolite ZSM-12 catalyst or zeolite ZSM-21 catalyst. The zeolite can be incorporated in an inert, and therefore non-acidic, alumina matrix. U.S. Pat. No. 3,856,872 contains no teaching on kind or amount of zeolite ZSM-21.

The article "Dealuminated zeolite-based composite catalysts for reforming of an industrial naphthene-rich feedstock" deals with reforming catalysts for naphthenic feedstocks. The preferred ZSM-12 zeolite has a Si/Al ratio of 54. It is taught that ZSM-12 having higher silica to alumina ratios should not be used for such catalysts as this produces large amounts of $CH_4$ and less aromatics.

An object of the present invention is to provide an improved catalyst for the isomerisation of alkylaromatics such as ethylbenzene and meta-xylene to provide xylenes especially para-xylene.

According to a first aspect of the present invention, there is provided an alkylaromatics isomerisation catalyst which catalyst comprises:
 at least 50 wt % of an acidic inorganic binder;
 at least 0.01 wt % of a Group VIII metal;
 1-9 wt % ZSM-12 zeolite;
wherein the ZSM-12 zeolite has a silica to alumina molar ratio (SAR) in the range of from 60 to 200. The weight amounts are on total weight of catalyst.

FIG. 1 presents plots of EB Conversion provided by the catalyst of Example 3 and two comparison catalysts for different WHSVs.

FIG. 2 presents plots of EB-ate of the catalyst of Example 3 and two comparison catalysts for different WHSVs.

FIG. 3 presents plots of wt % of C1-C5 made as the p-xylene approaches to equilibrium achieved with the catalyst of the present invention and a comparison catalyst.

FIG. 4 presents plots of wt % benzene made as the p-xylene approaches to equilibrium with the acatalyst of the present invention and a comparison catalyst.

FIG. 5 presents plots of ethylbenzene (EB) conversion versus weight hourly space velocity (WHSV) for the catalysts of the present invention compared with that of a comparison catalyst.

This particular combination of components has been found to be surprisingly beneficial in providing a catalyst for the isomerisation of alkylaromatics, especially in relation to alkylaromatics containing 8 carbon atoms.

This particular combination of components has been found to provide a catalyst for the isomerisation of alkylaromatics containing 8 carbon atoms which catalyst is able to:
 reduce side reactions such as the formation of compounds containing of from 1 to 5 carbon atoms, and thus any unwanted creation of carbon dioxide, and/or
 reduce the formation of benzene, and/or
 increase the conversion of ethylbenzene, and/or
 increase the production of other desired products such as para-xylene, and/or
 increase and/or improve the separation of desired product(s) from the reaction mixture, such as para-xylene.

One or more of the above provisions leads to an increase in the final yield of one or more of the desired products such as para-xylene.

The increase of ethylbenzene conversion is not only a desired advantage in its own right, but also reduces the amount of a major competitive absorbent in the reaction mixture for the subsequent separation. Separating para-xylene, in particular from a reaction mixture predominantly consisting of compounds containing 8 carbon atoms, by using molecular sieves is known to be difficult because of the presence of competitive absorbents, such as remaining ethylbenzene, which reduces the efficiency of the separation process. Thus, creating less competitive absorbents in the reaction mixture makes it significantly easier to separate the desired products such as para-xylene.

Some side products, such as toluene, benzene and aromatic compounds containing 9 or more carbon atoms, can also be useful commercial products, such that their formation in isomerisation of compounds containing 8 carbon atoms is still useful and not wholly undesired, but their formation is secondary to achieving increased ethylbenzene conversion and the advantages thereof.

The present invention is not limited to alkylaromatics containing 8 carbon atoms but includes the isomerisation of other alkylaromatics such as alkylaromatics containing 9 carbon atoms or more, including alkylaromatics containing 9 or 10 carbon atoms, which are known to follow similar reaction paths, and to use the same or similar catalyst formulations. Therefore, the present invention relates to isomerisation of alkylaromatics in general, more specifically alkylaromatics comprising of from 8 to 10 carbons, more specifically alkylaromatics comprising 8 or 9 carbon atoms.

The acidic inorganic binder may be selected from any of the suitable acidic refractory metal oxides known in the art. Examples of preferred acidic inorganic binders is alumina optionally in combination with other compounds such as silica, alumina, titania, zirconia, ceria and/or gallia. Preferably, the binder consists of alumina with up to 50% wt of other compounds, more specifically up to 20% wt, more specifically up to 10% wt, most specifically up to 5% wt. Preferably, the binder consists of acidic alumina.

Alumina can be prepared in a number of forms. The alumina grades available differ in parameters such as pore volume, average pore diameter, bulk density, and surface area. Although different alumina manufacturers can provide the same or similar alumina products under different nomenclature, different products classifications can have the same or similar or overlapping criteria and/or properties. For example, "high pore" and "wide pore" aluminas tend to have the same or similar properties.

The present invention extends to the use of alumina as the inorganic binder from any source, and examples of suitable alumina binders include grades of the Pural range from Sasol, such as the KR and SB grades, and other wide pore aluminas such as WPA from Criterion.

In a preferred embodiment of the present invention, the pore volume of the inorganic binder as measured with the help of nitrogen is at least 0.6 cc/g, preferably at least 1.2 cc/g; and the pore volume of the inorganic binder is up to 2 cc/g, preferably up to 1.6 cc/g.

These ranges of pore volume of the inorganic binder include 'wide pore' alumina, which has a more open structure to allow greater interaction with the alkylaromatics.

In another embodiment of the present invention, the average pore diameter of the inorganic binder is greater than 80 Å, preferably greater than 90 Å.

In a further embodiment of the present invention, the bulk density of the inorganic binder is less than 0.3, preferably less than 0.25 g/cc.

In a yet further embodiment of the present invention, the inorganic binder is present in the amount of more than 80 wt %, preferably more than 90 wt %, especially at least 95 wt %, based on total amount of catalyst.

A more open structure of the inorganic binder, based on one or more of parameters such as pore volume, pore diameter and bulk density, provide better diffusion of the reactant(s) reaching the catalytic material in the catalyst, and better diffusion of the product(s) away from the catalytic material. Greater reactant(s) and product(s) diffusion around the catalytic material increases the reaction rate and/or yield and/or purity.

The catalyst includes at least 0.01 wt % of a Group VIII metal of the Periodic Table of the Elements. The amount is the amount of metal on total weight of catalyst. Reference to "Group VIII" as used herein relates to the current IUPAC version of the Periodic Table. Preferred catalytically active metals are nickel, palladium and/or platinum. The most preferred metal is platinum. Combinations of two or more catalytically active metals are also possible, preferably being platinum metal combinations. The catalytically active metal may also be provided in the form of a compound, optionally requiring activation prior to use.

In one embodiment to the present invention, the Group VIII metal is present in the catalyst in an amount in the range of 0.1-0.6 wt % based on total weight of catalyst.

The zeolite ZSM-12 is a well known zeolite, generally having an aluminosilicate basis, optionally including one or more other elements. Many methods of making various forms of ZSM-12 are known in the art. By way of example only, WO 2004/046034 provides a discussion of the formation of certain forms of ZSM-12, and is included herein by way of reference.

The catalyst could be provided by admixture of the inorganic binder and zeolite components, following by shaping, and then typically drying and calcining the pre-former product. Optionally, the addition of the Group VIII metal is carried out after drying and/or calcining of the catalyst pre-former, and optionally there is a further calcination thereafter. Preferably, the catalyst is prepared by extrusion. Therefore, the catalyst preferably is an extrudate.

It is known that the crystal morphology of a zeolite influences its activity and stability. In the present invention, it is particularly preferred that the ZSM-12 zeolite has:

an average crystal size in the range of 30 to 70 nm; and/or a surface area as measured with the help of nitrogen adsorption of more than 250 m$^2$/g, preferably more than 280 m$^2$/g; and/or a crystallinity greater than 94%, preferably greater than 97%.

The provision of a zeolite having defined parameters such as those described above in relation to zeolite crystal morphology is known to those skilled in the art and is not further described herein.

The proportion of the catalyst being the ZSM-12 zeolite is preferably in the range 1-7 wt %, preferably 1-5 wt %, especially 3-5 wt %, based on total amount of catalyst. Whilst the catalyst of the present invention may include a minor or very small amount zeolites other than ZSM-12, the catalyst preferably comprises only ZSM-12 as the zeolite.

Another parameter of the zeolite ZSM-12 is its silica to alumina molar ratio (SAR). In the ethylbenzene reforming process, two different reactions overlap: ethylbenzene isomerisation and xylene isomerisation. Both reactions need acid sites to occur, and the acidity of the zeolite has therefore always conventionally been considered as having to be moderate. For this reason, conventional commercial catalysts have low SAR, and conventionally, it has been desired to maintain a relatively low SAR. The skilled person is not directed in the art to considering using a high SAR in a catalyst and prior art ZSM-12 based catalysts generally have a low SAR. For example, the SAR of the comparison catalysts 1 and 2 described hereinafter are both 30.

It is a particular feature of the present invention that the SAR of the zeolite is in the range of from 60 to 200, preferably in the range 70 to 150. This is because of the recognition that the acidity of the zeolite is not the only factor that will determine the performance of a catalyst. Inorganic binders such as those based on alumina are also acidic, and so will contribute to the reaction as well. Similarly, it is generally expected that a higher loading of zeolite in the catalyst will increase the catalyst activity and/or yield, so that the skilled person is directed in the art to considering having a significant proportion of the catalyst being the zeolite component such as more than 10 wt %.

It is another particular feature of the present invention to provide a catalyst having a lower than expected zeolite proportion, most especially at most 9 wt %, and in particular less than 5 wt % based on total amount of catalyst.

Thus, although the present invention provides a catalyst having a lower than expected proportion of zeolite, and a higher than expected SAR in the zeolite, nevertheless the catalyst provided by the present invention has been found to be particularly beneficial in the isomerisation of alkylaromatics.

The alkylaromatics isomerisation catalyst preferably consists of acidic inorganic binder, ZSM-12 zeolite having a SAR of from 60 to 200 and a Group VIII metal in the amount described above.

The catalyst of the present invention is particularly suitable for the hydroisomerisation of ethylbenzene to xylenes, and for the isomerisation of xylenes to equilibrium. Further particularly, the catalyst of the present invention is suitable for use to provide para-xylene from ethylbenzene and other isomers of xylene commonly provided in mixed-component streams.

According to a second aspect of the present invention, there is provided a process for the isomerisation of alkylaromatics to provide a reaction mixture, which process comprises contacting a hydrocarbon stream comprising alkylaromatics with a catalyst as defined above.

The hydrocarbon stream may comprise any amount of ethylbenzene, such as more than 60 wt % based on total amount of feedstock. The hydrocarbon stream specifically contains at most 60 wt % of ethylbenzene, more specifically at most 50% wt. Preferably, the hydrocarbon stream comprises at least 1% wt of ethylbenzene, more preferably at least 2 % wt, more preferably at least 3 % wt, more specifically at least 5% wt, more specifically at least 8 % wt, preferably at least 10% wt, most preferably at least 15 wt %.

In one embodiment of the process of the present invention, the hydrocarbon stream is contacted with the catalyst at a temperature in the range of from 300 to 450° C., preferably at least 350° C. and preferably at most 400° C.

In another embodiment, preferably at least 20% of the ethylbenzene in the feed is converted into xylenes, more specifically at least 25%, more specifically at least 30%, more specifically at least 35% an most specifically at least 40%.

In a further embodiment, the ratio of para-xylene to ethylbenzene in the reaction mixture obtained is more than 1.3, preferably more than 1.5 and most preferably more than 2.

According to a third aspect of the present invention, there is provided use of a catalyst as defined herein to reduce the amount of compounds containing of from 1 to 5 carbon atoms created in a process for the isomerisation of aromatics from a hydrocarbon stream comprising ethylbenzene.

Examples of the present invention will now be described by way of example only.

PREPARATION EXAMPLES

Example 1

A ZSM-12/alumina catalyst was prepared from 5 wt % of ZSM-12 having a SAR of 95, and 95 wt % of Sasol Pural SB3 alumina.

The mixture was kneaded and then shaped by extrusion into 1.6 mm cylinders. The extrudates were then dried at 120° C. and subsequently calcined in air at 550° C. for 4 hours. The finished extrudates were then subject to a pore volume impregnation with the help of a platinum containing solution to obtain extrudates comprising 0.3 wt % Pt followed by drying at 120° C. and calcination at 450° C. for 4 hours. No further treatment was done on the catalyst.

Example 2

The catalyst prepared in Example 1 was tested in the isomerisation of an ethylbenzene and mixed xylene mixture (comprising 19 wt % ethylbenzene (EB), 15.5 wt % ortho-xylene (OX), 59 wt % meta-xylene (MX) and 6.5 wt % ethyl cyclohexane).

The catalytic test was performed in a micro-flow reactor unit encompassing a reactor tube with an internal diameter of 15 mm, into which the catalyst was loaded together with SiC as packing material. After loading the catalyst was dried at 400° C. for 1.5 hours and then reduced with $H_2$ at 400° C. for 1 hour at a pressure of 8 bar. The reactor was then heated to 425° C. and treated with a mixture of 20 wt % EB and 80 wt % meta-xylene for a period of 24 hours at a weight hourly space velocity (WHSV) of 5 g feed/g catalyst/h and a $H_2$/hydrocarbon ratio of 4 mol/mol to reach a stable operation regime. Following this, the catalyst was subjected to a temperature of 387° C. and treated with the same EB and mixed xylene mixture described above (19 wt % EB, 15.5 wt % OX, 59 wt % MX, 6.5 wt % ethyl cyclohexane) at a WHSV of 3.5 g feed/g catalyst/h and a $H_2$/hydrocarbon ratio of 4 mol/mol.

The results can be seen in Table 1, which shows the wt % of ethylbenzene converted (EBC), the final wt % of para-xylene found in the xylene mixture (pX in xyl), and the wt % of the starting compounds having 8 carbon atoms being converted into undesired end products ("C8 ring loss").

TABLE 1

| Conditions | |
| --- | --- |
| T (° C.) | 386.6 |
| WHSV (g feed/g catalyst/h) | 3.5 |
| $H_2$/hydrocarbon (mol/mol) | 4 |
| Pressure (barg) | 7.6 |
| Performance | |
| EBC (%) | 55.65 |
| pX in Xyl (%) | 23.97 |
| C8 ring loss (wt %) | 11.31 |
| Product Breakdown | |
| C1-C5 | 4.15 |
| C6+ not aromatic | 6.51 |
| Benzene | 0.58 |
| Toluene | 2.75 |
| Ethylbenzene | 8.44 |
| Para-Xylene | 17.67 |
| Meta-Xylene | 39.21 |
| Ortho-Xylene | 16.85 |
| C9+ Aromatics | 3.84 |

Example 3

A ZSM-12/alumina catalyst was prepared from 5 wt % of ZSM-12 having a SAR of 95, and 95 wt % of wide pore alumina (Sasol, KRII alumina). The mixture was kneaded and then shaped by extrusion into 1.6 mm cylinders. The extrudates were then dried at 120° C. and subsequently calcined in air at 550° C. for 4 hours. The finished extrudates were then subject to a pore volume impregnation with the help of a platinum containing solution to obtain extrudates comprising 0.3 wt % Pt followed by drying at 120° C. and calcination at 450° C. for 4 hours. No further treatment was done on the catalyst.

Example 4

The catalyst prepared in Example 3 was tested in the isomerisation of an EB and mixed xylene mixture (19 wt % EB, 15.5 wt % OX, 59 wt % MX, 6.5-wt % ethyl cyclohexane). The catalytic test was performed in a micro-flow reactor unit encompassing a reactor tube with an internal diameter of 15 mm, into which the catalyst was loaded together with SiC as packing material. After loading the catalyst was dried at 400° C. for 1.5 hours and then reduced with $H_2$ at 400° C. for 1 hour at a pressure of 8 bar. The reactor was then heated to 425° C. and treated with a mixture of 20 wt % EB and 80 wt % meta-xylene for a period of 24 hours at a WHSV of 5 g feed/g catalyst/h and a $H_2$/hydrocarbon ratio of 4 mol/mol to reach a stable operation regime. Following this, the catalyst was subjected to a temperature of 387° C. and treated with the same EB and mixed xylene mixture (of 19 wt % EB, 15.5 wt % OX, 59 wt % MX, 6.5 wt % ethyl cyclohexane) at a WHSV of 3.5 g feed/g catalyst/h and a $H_2$/hydrocarbon ratio of 4 mol/mol. The results can be seen in Table 2.

TABLE 2

| Conditions | |
|---|---|
| T (° C.) | 386.6 |
| WHSV (g feed/g catalyst/h) | 3.5 |
| $H_2$/hydrocarbon (mol/mol) | 4 |
| Pressure (barg) | 7.6 |
| Performance | |
| EBC (%) | 40.47 |
| pX in Xyl (%) | 23.60 |
| C8 ring loss (wt %) | 3.26 |
| Product Breakdown | |
| C1-C5 | 0.87 |
| C6+ not aromatic | 6.96 |
| Benzene | 0.17 |
| Toluene | 0.92 |
| Ethylbenzene | 11.36 |
| Para-Xylene | 18.51 |
| Meta-Xylene | 41.89 |
| Ortho-Xylene | 18.05 |
| C9+ Aromatics | 1.27 |

Example 5

A ZSM-12/alumina catalyst was prepared from 10 wt % of ZSM-12 having a SAR of 95 and 90 wt % of wide pore alumina (Sasol, KRII alumina). The mixture was kneaded and then shaped by extrusion into 1.6 mm cylinders. The extrudates were then dried at 120° C. and subsequently calcined in air at 550° C. for 4 hours. The finished extrudates were then subject to a pore volume impregnation with the help of a platinum containing solution to obtain extrudates comprising 0.3 wt % Pt followed by drying at 120° C. and calcination at 450° C. for 4 hours. No further treatment was done on the catalyst.

Example 6

The catalyst prepared in Example 5 was tested in the isomerisation of an EB and mixed xylene mixture (19 wt % EB, 15.5 wt % OX, 59 wt % MX, 6.5 wt % ethyl cyclohexane). The catalytic test was performed in a micro-flow reactor unit encompassing a reactor tube with an internal diameter of 15 mm, into which the catalyst was loaded together with SiC as packing material. After loading the catalyst was dried at 400° C. for 1.5 hours and then reduced with $H_2$ at 400° C. for 1 hour at a pressure of 8 bars. The reactor was then heated to 425° C. and treated with a mixture of 20 wt % EB and 80 wt % meta-xylene for a period of 24 hours at a WHSV of 5 g feed/g catalyst/h and a $H_2$/hydrocarbon ratio of 4 mol/mol to reach a stable operation regime. Following this, the catalyst was subjected to a temperature of 387° C. and treated with the same EB and mixed xylene mixture (19 wt % EB, 15.5 wt % OX, 59 wt % MX, 6.5 wt % ethyl cyclohexane) at a WHSV of 3.5 g feed/g catalyst/h and a $H_2$/hydrocarbon ratio of 4 mol/mol. The results can be seen in Table 3.

TABLE 3

| Conditions | |
|---|---|
| T (° C.) | 386.4 |
| WHSV (g feed/g catalyst/h) | 3.5 |
| $H_2$/hydrocarbon (mol/mol) | 4.0 |
| Pressure (barg) | 7.6 |
| Performance | |
| EBC (%) | 55.03 |
| pX in Xyl (%) | 23.93 |
| C8 ring loss (wt %) | 7.77 |
| Product Breakdown | |
| C1-C5 | 2.66 |
| C6+ not aromatic | 7.30 |
| Benzene | 0.30 |
| Toluene | 1.93 |
| Ethylbenzene | 8.57 |
| Para-Xylene | 18.30 |
| Meta-Xylene | 40.80 |
| Ortho-Xylene | 17.38 |
| C9+ Aromatics | 2.75 |

Alumina Examples

Table 4 provides parameters for four alumina inorganic binders which may be used by the present invention. Pural Kr II is a high-pore alumina available from Sasol. Pural SB3 is a low pore alumina also available from Sasol. WPA ("wide pore alumina") is available from Criterion.

TABLE 4

| Feature | Pural KR II | Pural SB3 | WPA |
|---|---|---|---|
| Average bulk density (g/cc) | 0.315 | 0.76 | 0.2 |
| Pore volume (cc/g) | 1.4 | 0.5 | 1 |
| Average surface area (m2/g) | 290 | 255-260 | 345 |

Comparison Examples

Table 5 shows a comparison of the catalyst of Example 3 against a comparison catalyst 1 and a comparison catalyst 2, using the same reaction conditions as described in Preparation Examples 4 and 6 herein above based on a WHSV of 3.5 g feed/g catalyst/h. All the parameters of the comparisons are expressed at a pX-ate of 95%.

Comparison catalyst 1 comprised 10.5 wt % of a commercial zeolite EU-1 of structure type EU0 as described in EP 6,057,486 A1, having a pore diameter of 4.1×5.7 Å, and 89.2 wt % of the commercial binder Pural SB3 having an SAR ratio of 30, 0.3 wt % of Pt.

Comparison catalyst 2 comprised 9 wt % of the same commercial zeolite EU-1, and 90.7 wt % of the commercial binder Pural KR II, also having an SAR ratio of 30, and 0.3 wt % Pt.

The three catalysts were compared for their:
(a) Ethylbenzene Conversion ("EBC" or "EB conversion"), i.e. the weight percent of ethylbenzene converted by the catalyst into a xylene;
(b) "EB-ate" (i.e. their ethylbenzene approaching to equilibrium); and
(c) "C8R loss" (i.e. their C8 ring loss).

TABLE 5

| Performance parameter | | Example 3 | Comparison catalyst 1 | Comparison catalyst 2 |
|---|---|---|---|---|
| EBC (%) | | 32 | 15 | 14 |
| EB-ate (wt %) | | 46 | 20 | 19 |
| C8R loss (mole %) | Overall | 2.4-2.6 | 2.4-2.6 | 1.8-2.0 |
| | C1-C5 Gas (wt %) | 0.61 | 1.12 | 0.95 |
| | Toluene (wt %) | 0.69 | 0.55 | 0.29 |
| | C9+ aromatics (wt %) | 0.95 | 0.62 | 0.55 |
| | Benzene (wt %) | 0.34 | 0.14 | 0.24 |

As Table 5 shows, the catalyst of Example 3 above has a more than double increase in ethylbenzene conversion and significantly higher EB-ate.

Table 6 shows a comparison of the amounts of para-xylene and ethylbenzene in the product reaction mixture, and their ratio (PX/EB) (see Table 2), from the use of the catalyst of the present invention according to Preparation Examples 1, 3 and 5 described above in Tables 1, 2 and 3, and the use of the two comparison catalyst 1 and 2 (referred to as "Compare 1" and " Compare 2" respectively) also described above, under the same reaction conditions described in Preparation Example 4 hereinabove.

TABLE 6

| Catalyst | PX (wt %) in the product | EB (wt %) in the product | PX/EB |
|---|---|---|---|
| Example 1 | 17.67 | 8.44 | 2.09 |
| Example 3 | 18.51 | 11.36 | 1.63 |
| Example 5 | 18.30 | 8.57 | 2.14 |
| Compare 1 | 17.89 | 14.55 | 1.23 |
| Compare 2 | 18.11 | 14.58 | 1.24 |

Whilst the same or only a small increase in the amount of para-xylene was obtained by the use of the catalysts of the Examples of the present invention, the significantly lower amounts of ethylbenzene in the product mixture leads (a) to a significantly increased PX/EE ratio on an industrial scale, and (b) to significantly easier separation of the para-Xylene from the product mixture by the reduced interference in the separation process of the competitive absorbent ethylbenzene.

The catalyst of Preparation Example 3 also increases the amount of toluene and C9+ aromatics produced, which are also useful commercial products, whilst decreasing the (undesired) C1-C5 gas formation.

Table 7 shows a comparison of the amount of C1-C5 produced from the use of the catalyst of Preparation Example 3 and the use of the two comparison catalyst 1 and 2 (referred to as "Compare 1" and " Compare 2" respectively) at a pX-ate of 95 wt % per gram catalyst.

TABLE 7

| Catalyst | C1-C5 wt % | Average $CO_2$ emission wt % | Minimum level $CO_2$ | Maximum level $CO_2$ |
|---|---|---|---|---|
| Example 3 | 0.60 | 1.80 | 1.76 | 1.82 |
| Compare 1 | 1.15 | 3.45 | 3.37 | 3.49 |
| Compare 2 | 0.95 | 2.85 | 2.78 | 2.88 |

Table 7 shows a significant reduction in the amount of C1-C5 compounds created, which would significantly reduce the amount of $CO_2$ created if the C1-C5 compounds were flared as also shown in Table 7. The minimum and maximum levels of $CO_2$ in Table 7 represent estimated variations in the amount of $CO_2$ depending on creating a greater proportion of lighter C1-C5 compounds, such as C2, creating a minimum level, or a greater proportion of heavier C1-C5 compounds, such as C4, creating a maximum level. The comparison of these catalysts over a range of parameters and WHSVs can also be seen graphically with reference to the accompanying figures in which:

Table 8 below shows a summary of certain comparisons between Preparation Examples 3 and 5 herein above, as well as an intermediate example based on 7 wt % of the same ZSM-12 zeolite, and the above Comparison catalyst 1.

TABLE 8

| | | | | Comparison Catalyst 2 |
|---|---|---|---|---|
| Catalyst composition | | | | |
| wt % zeolite | 5 | 7 | 10 | 9 |
| wt % KRII binder | 95 | 93 | 90 | 90.7 |
| Preparation Example | 3 | | 5 | |

TABLE 8-continued

| Catalyst Performance | | | | Comparison Catalyst 2 |
|---|---|---|---|---|
| EBC at pX-ate 95 | 32 | 32 | 30 | 15 |
| C8R loss (mole %) | 2.5 | 2.5 | 2.6 | 2.5 |

Figure 1:
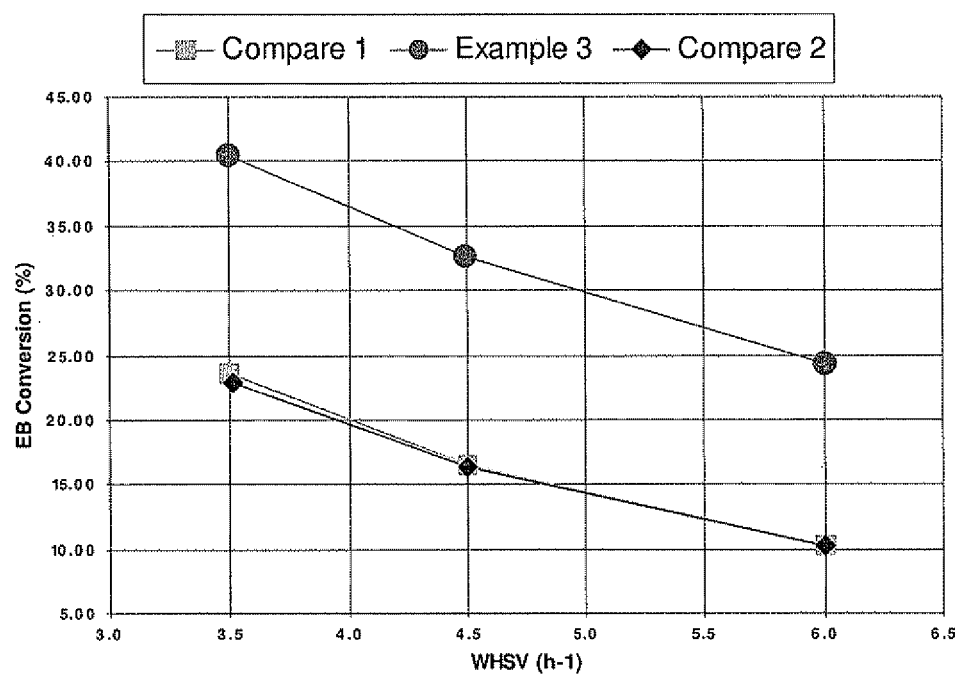
FIG. 1 shows the superior EB Conversion of the catalyst of Example 3 over the two comparison catalysts mentioned above (again labelled "Compare 1" and "Compare 2") over different WHSVs.
Figure 2:
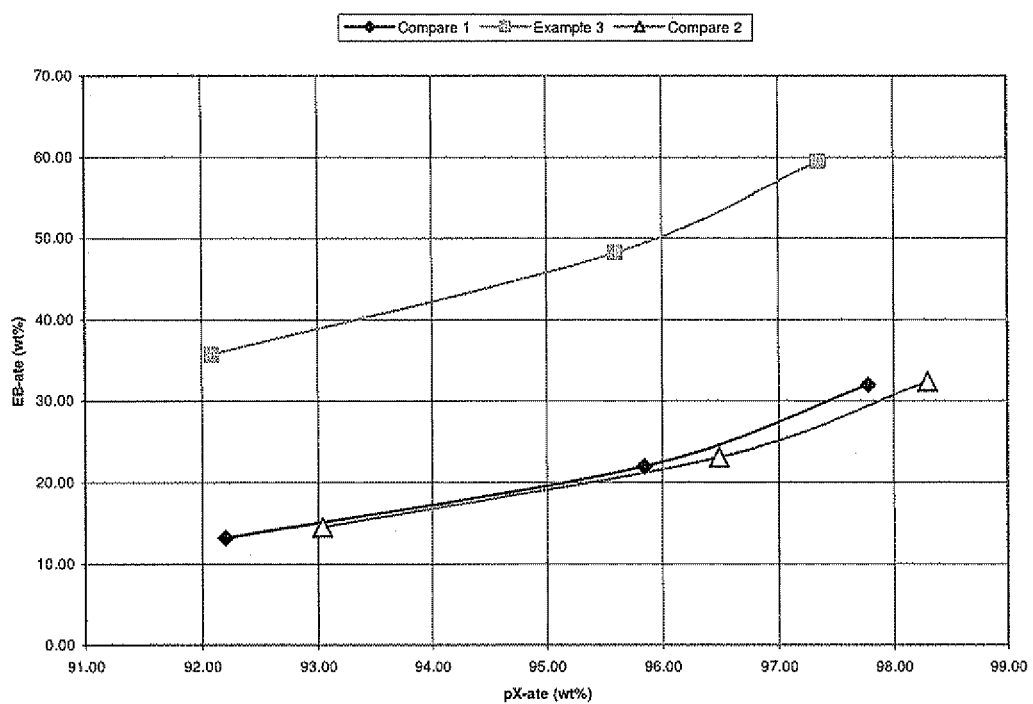
FIG. 2 shows the superior EB-ate of the catalyst of Example 3 over the same two comparison catalysts over different WHSVs.
Figure 3:
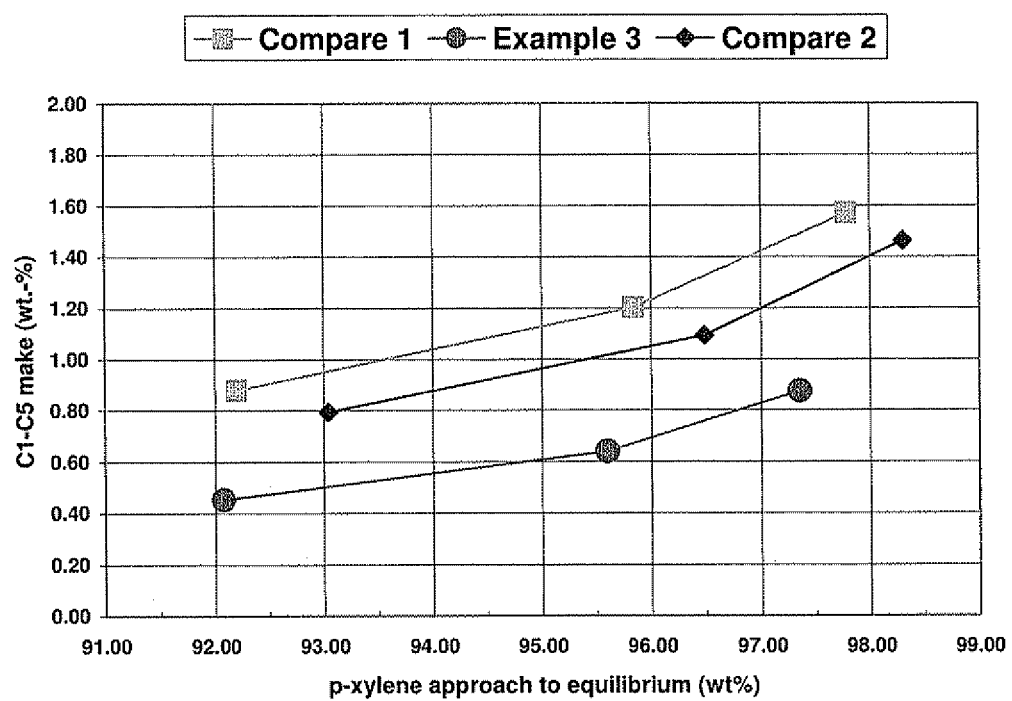
FIG. 3 shows the superior decrease in wt % of C1-C5 made as the p-xylene approaches to equilibrium is achieved under the same reaction conditions. The catalyst of the present invention creates significantly less C1-C5 products, which has the further advantage that less gas, in particular carbon dioxide, is made if such products were flared.
Figure 4:
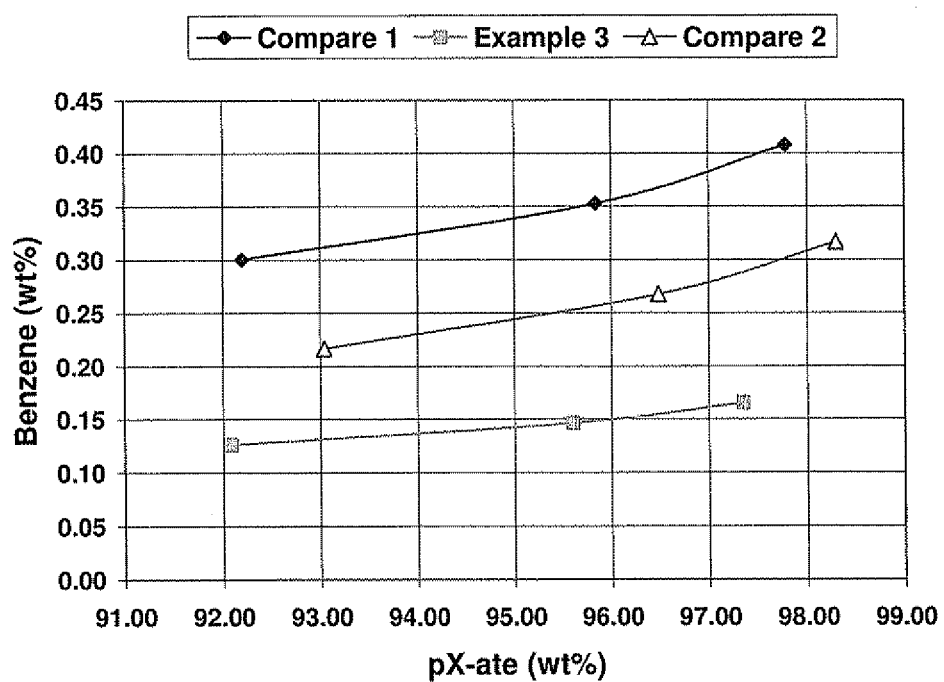
FIG. 4 shows the superior decrease in wt % of benzene made as the p-xylene approaches to equilibrium is achieved under the same reaction conditions. Benzene is a by-product of C8 isomerisation usually not desired in this process.
Figure 5:
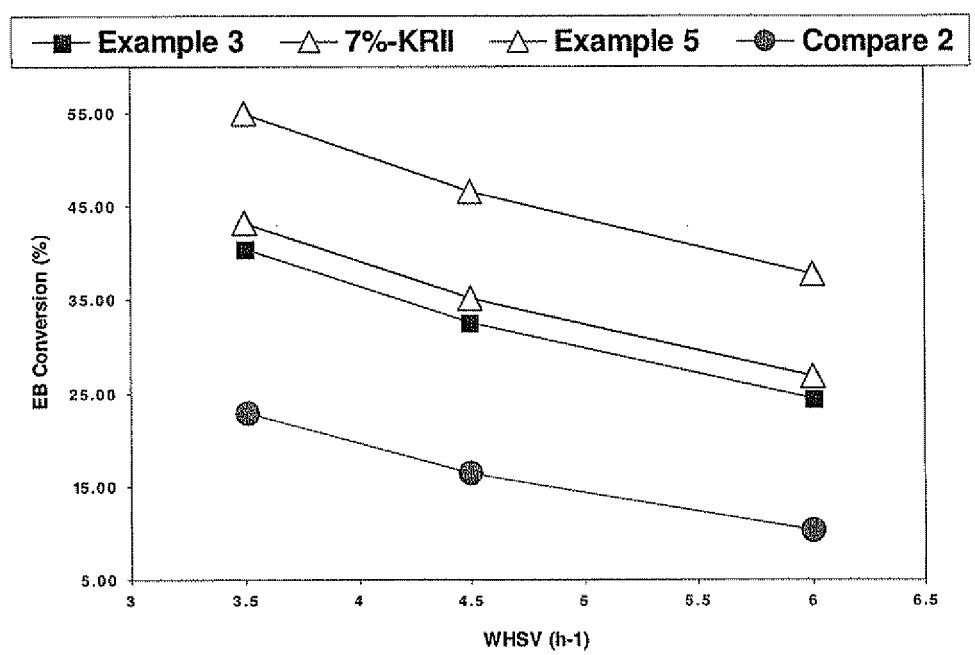

The comparison of these catalysts can also be seen graphically with reference to FIG. 5 which shows a graph of the superior ethylbenzene (EB) conversion versus weight hourly space velocity (WHSV) for the catalysts of the present invention compared with that of Comparison Catalyst 2 having a similar weight of the same binder, but a different zeolite.

The above data and examples confirm that catalysts prepared according to the present invention do not require additional components such as magnesium, chlorine or lead to isomerise alkylaromatics, unlike prior art catalysts. Thus, the catalysts of the present invention are simpler to prepare and require less forming steps.

The above data and examples also confirm that relatively low amounts of zeolite can be used to provide the same or better performance in the isomerisation of alkylaromatics, thus reducing CAPEX and OPEX costs for such commercial operations.

The above data and examples also confirm that the specific use of ZSM-12 with a relatively high SAR ratio can improve the product yield and/or reduce the yield of side products, in particular the conversion of ethylbenzene to provide para-xylene.

The person skilled in the art will understand that the present invention can be carried out in many various ways without departing from the scope of the appended claims.

That which is claimed is:

1. An ethylbenzene conversion catalyst, which catalyst comprises:
   more than 90 wt % of a wide pore alumina binder having a pore volume of at least 0.6 cc/g up to 2 cc/g and an average pore volume greater than 80 Å;
   platinum metal in an amount in the range of from 0.1 to 0.6 wt % based on the total weight of said catalyst;
   from 1 to 9 wt % ZSM-12 zeolite having a silica to alumina molar ratio (SAR) in the range of from 60 to 200; and
   an absence of lead.

2. A catalyst as claimed in claim 1, wherein the catalyst is an extrudate.

3. A catalyst as claimed in claim 2, wherein the pore volume of the inorganic binder is at least 1.2 cc/g.

4. A catalyst as claimed in claim 3, wherein the bulk density of the inorganic binder is less than 0.25 g/cc.

5. A catalyst as claimed in claim 4, wherein the SAR of the ZSM-12 zeolite is in the range of from 70 to 150.

6. A catalyst as claimed in claim 5, which catalyst comprises 1-7 wt % ZSM-12 zeolite.

7. A catalyst as claimed in claim 6, wherein the ZSM-12 zeolite has an average crystal size in the range of 30 to 70 nm.

8. A catalyst as claimed in claim 7, wherein the ZSM-12 zeolite has a crystallinity greater than 94%.

9. An alkylaromatics isomerization catalyst, comprising:
   more than 80 wt % of a wide pore alumina binder having a pore volume of at least 0.6 cc/g up to 2 cc/g and an average pore volume greater than 80 Å;
   platinum in an amount in the range of from 0.1 to 0.6 wt %;
   from 1 to 9 wt %, based on the total weight of said catalyst, zeolite ZSM-12 having a silica-to-alumina molar ratio (SAR) in the range of from 60 to 200;
   an absence of lead; and
   an absence of chlorine.

10. An alkylaromatics isomerization catalyst as recited in claim 9, wherein said wide pore alumina binder has a nitrogen pore volume of at least 1.2 cc/g and up to 2 cc/g.

11. An alkylaromatics isomerization catalyst as recited in claim 9, wherein the crystal morphology of said zeolite ZSM-12 is such that it has an average crystal size in the range of from 30 to 70 nm, a surface area of more than 250 $m^2/g$ measured by the nitrogen adsorption method, and a crystallinity of greater than 94%.

12. An alkylaromatics isomerization catalyst as recited in claim 9, wherein said wide pore alumina binder has an average pore diameter greater than 90 Å.

13. An alkylaromatics isomerization catalyst as recited in claim 9, wherein said zeolite ZSM-12 has a SAR in the range of from 70 to 150.

14. An alkylaromatics isomerization catalyst as recited in claim 9, wherein said wide pore alumina binder is present in said catalyst in an amount of more than 90 wt %, based on the weight of said catalyst.

15. An alkylaromatics isomerization catalyst as recited in claim 9, wherein said zeolite ZSM-12 is present in said catalyst in an amount in the range of from 1 to 7 wt %.

16. An alkylaromatics isomerization catalyst as recited in claim 9, said surface area of said zeolite ZSM-12 is of more than 280 $m^2/g$.

17. An alkylaromatics isomerization catalyst as recited in claim 9, wherein said zeolite ZSM-12 is present in said catalyst in an amount in the range of from 3 to 5 wt %, wherein said alumina is present in said catalyst in an amount of more than 95 wt %.

18. An alkylaromatics isomerization catalyst as recited in claim 9, wherein said wide pore alumina binder has a bulk density less than 0.25 g/cc.

19. A catalyst as claimed in claim 1, wherein the catalyst additionally comprises an absence of chlorine.

* * * * *